United States Patent [19]

German

[11] Patent Number: 5,292,249
[45] Date of Patent: Mar. 8, 1994

[54] ADJUSTABLE ALIGNING REEL AND METHODS FOR ALIGNING A TOOTH

[76] Inventor: Daniel S. German, 689 Dell Ridge Dr., Dayton, Ohio 45429

[21] Appl. No.: 878,450

[22] Filed: May 4, 1992

[51] Int. Cl.⁵ .............................................. A61C 3/00
[52] U.S. Cl. ........................................ 433/22; 433/21; 433/24
[58] Field of Search ..................... 433/18, 19, 20, 21, 433/22, 23, 24

[56] References Cited

U.S. PATENT DOCUMENTS

| | | | |
|---|---|---|---|
| 3,654,703 | 4/1972 | Kelly, Jr. | 433/19 |
| 3,835,538 | 9/1974 | Northcutt | 433/24 |
| 3,921,295 | 11/1975 | James | 433/21 |
| 4,074,433 | 2/1978 | Nelson | 433/21 |
| 4,187,610 | 2/1980 | Ziegler | 433/24 |
| 4,483,674 | 11/1984 | Schultz | 433/22 |

*Primary Examiner*—John J. Wilson
*Attorney, Agent, or Firm*—Biebel & French

[57] ABSTRACT

An adjustable aligning reel for aligning a misaligned tooth into a predetermined position in an arch of teeth. The adjustable aligning reel comprises an adjustable tensioner which is capable of being mounted on an archwire in operative relationship with the misaligned tooth. The adjustable tensioner comprises a drive shaft having a filament attached thereto. An end of the filament is secured to a bracket which is mounted on the misaligned tooth and the drive shaft is rotated such that a predetermined tension is applied to the tooth. This tension causes the misaligned tooth to be moved towards the predetermined position. The drive shaft comprises a slip gear for preventing the tension applied to the filament from exceeding a preselected tension limit. The adjustable tensioner also includes a ratchet and pawl mechanism for preventing the drive shaft from rotating in a manner that causes the filament to unwind. A keyhole is provided at one end of the drive shaft to facilitate using a tool to rotate the drive shaft and tighten the filament.

34 Claims, 4 Drawing Sheets

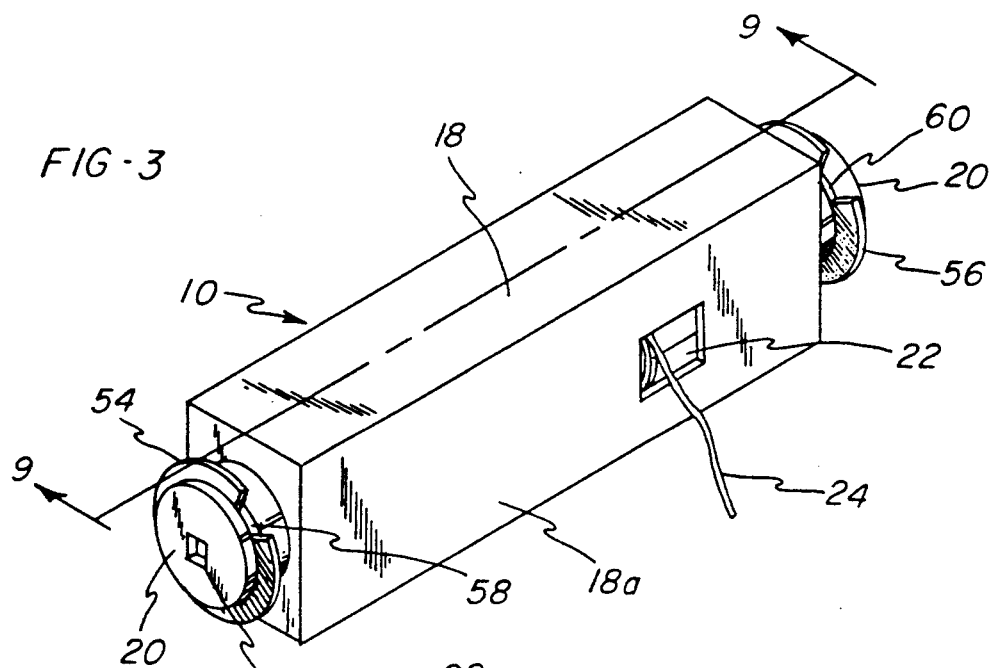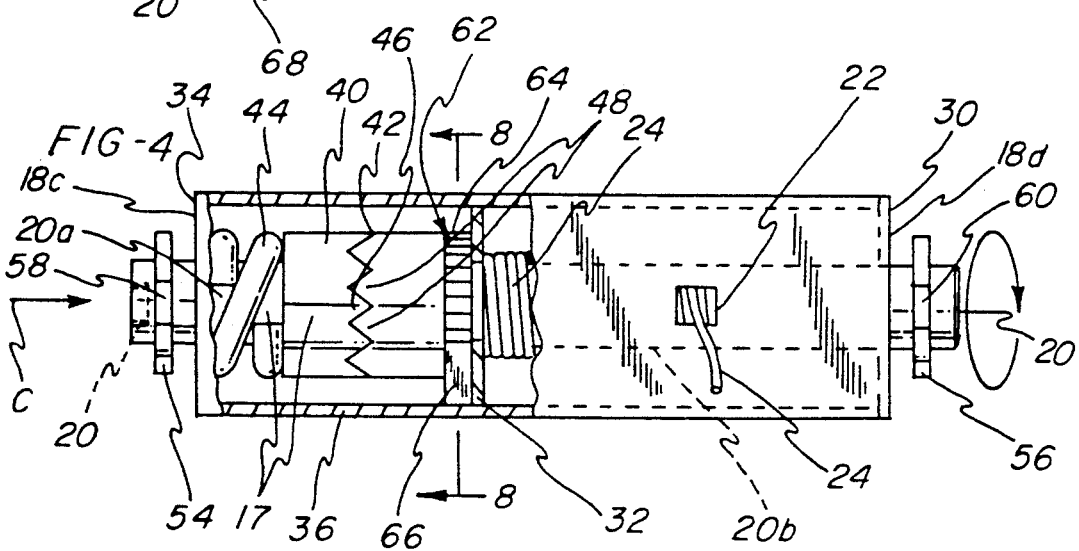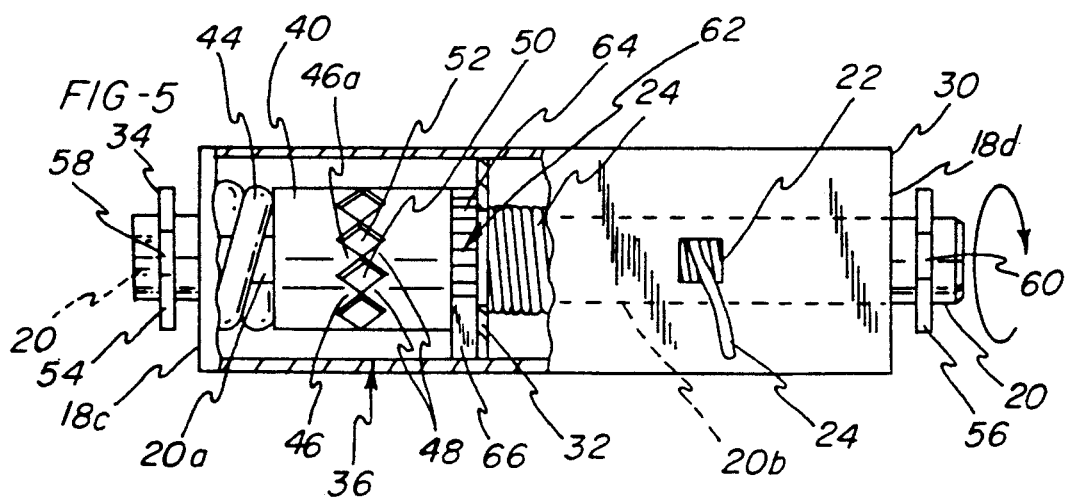

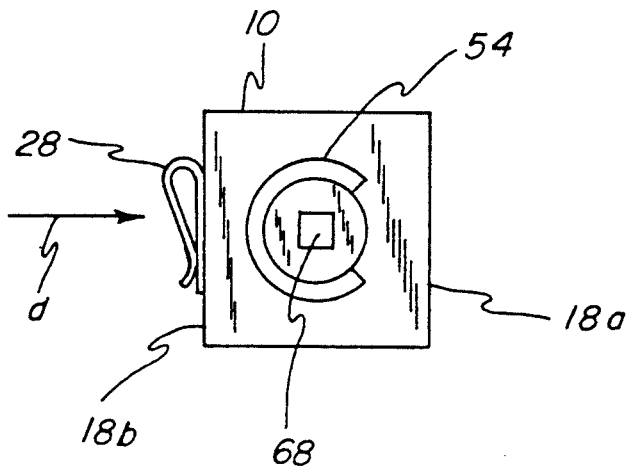
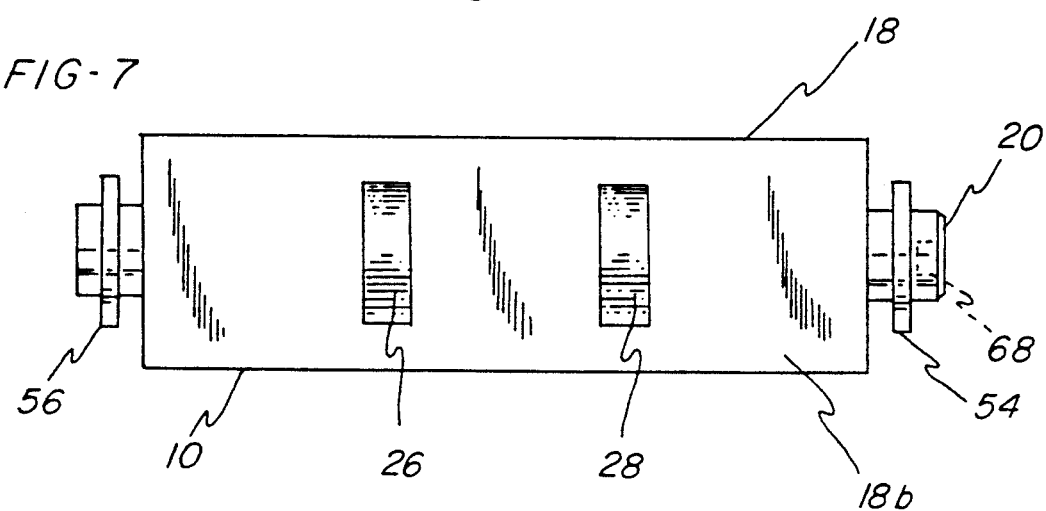
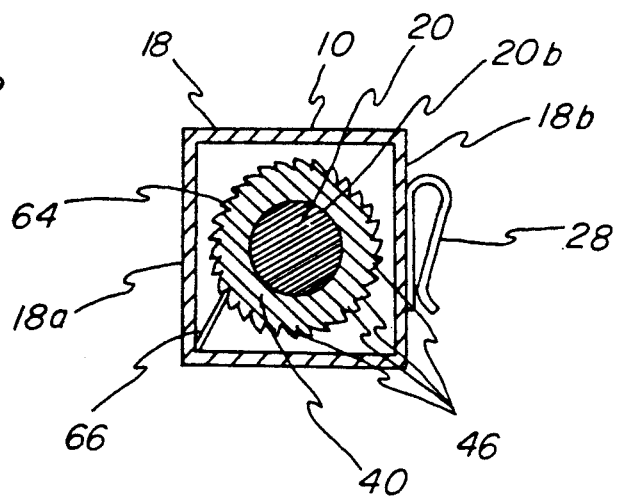

ADJUSTABLE ALIGNING REEL AND METHODS FOR ALIGNING A TOOTH

BACKGROUND OF THE INVENTION

1. Field of the Invention

This invention relates to a device for orthodontic tooth alignment, and more particularly, it relates to an adjustable aligning reel for aligning a tooth into a predetermined position in an arch of teeth.

2. Description of Related Art

In the field of orthodontics, it is often desirable or necessary to move a tooth, such as an impacted canine tooth, into an arch of teeth in a patient's mouth. In the past, a force was applied to the misaligned tooth by a rubber elastic or a wire having one end affixed to the tooth and another end coupled to an arch wire which was typically mounted around the arch of teeth. The movement of the tooth was accomplished in large part by rapid movement of the tooth which occurred immediately following visits with an orthodontist who would, for example, tighten the wire. During most of the time between visits with an orthodontist the patient's misaligned tooth was not being moved towards the arch of teeth. Another problem with the methods used in the prior art is that the patient had to visit the orthodontist regularly so that the orthodontist could either replace the rubber elastic or adjust the tension of the wire.

SUMMARY OF THE INVENTION

It is, therefore, an object of the present invention to provide an adjustable aligning reel for aligning a tooth into a predetermined position in an arch of teeth.

In one aspect of the invention, there is provided an adjustable aligning reel for aligning a tooth into a predetermined position in an arch of teeth, said aligning reel comprising an adjustable tensioner which is capable of being mounted on an archwire in operative relationship with the tooth; and a filament for coupling the misaligned tooth to said adjustable tensioner; said adjustable tensioner being adjustable to cause the filament to be tightened to a predetermined tension in order to pull the tooth towards the predetermined position.

In another aspect of the invention, there is provided a method of moving a tooth into a predetermined position in an arch of teeth, said method comprising the steps of: (a) mounting an adjustable tension reel on an arch wire associated with said arch of teeth; said adjustable tension reel having a filament which can be reeled into said adjustable tension reel; (b) mounting an end of said filament to said tooth; and (c) reeling said filament into said adjustable tension reel so as to pull said tooth towards said predetermined position.

An advantage of this invention is that it permits the patient to adjust the tension applied to a tooth in order to move the tooth into a predetermined position in an arch of teeth.

Another advantage of this invention is that it provides an adjustable aligning reel which can be mounted on and used with a conventional arch wire.

Another advantage of this invention is that it provides an adjustable aligning reel that can be reused.

Yet another advantage of this invention is that it permits a smaller magnitude of force to be applied to a misaligned tooth over a longer period of time.

Still another advantage of this invention is that it is compact in structure.

Another advantage of this invention is that the tension applied to the misaligned tooth can be adjusted.

Another advantage of this invention is that it includes means for preventing an excessive amount of tension from being applied to the tooth.

An object of this invention is to provide an adjustable aligner reel having an adjustable tensioner which is easily mounted on an arch wire.

Additional advantages, objects and features will become apparent from a reading of the following specification, drawing, and claims.

BRIEF DESCRIPTION OF THE DRAWING

FIG. 3 is a general perspective view of the adjustable aligning reel, showing the aperture for permitting the filament to pass through a housing;

FIG. 4 is a partly broken away side view, taken in the direction of arrow B in FIG. 3, showing a drive shaft having a slip gear portion comprising a first gear member which mates with a second gear member;

FIG. 5 is a view similar to that shown in FIG. 4 showing the first gear member disengaging the second gear member after the drive shaft has been tightened beyond a predetermined tension limit;

FIG. 6 is an end view, taken in the direction of arrow C in FIG. 4, showing a keyhole for turning the drive shaft;

FIG. 7 is a view taken in the direction of arrow D in FIG. 6, showing tie wings used for mounting the adjustable aligning reel onto the archwire;

FIG. 8 is a view, taken along the line 8—8 in used to prevent the filament from unwinding;

DESCRIPTION OF THE PREFERRED EMBODIMENT

Figure 1:
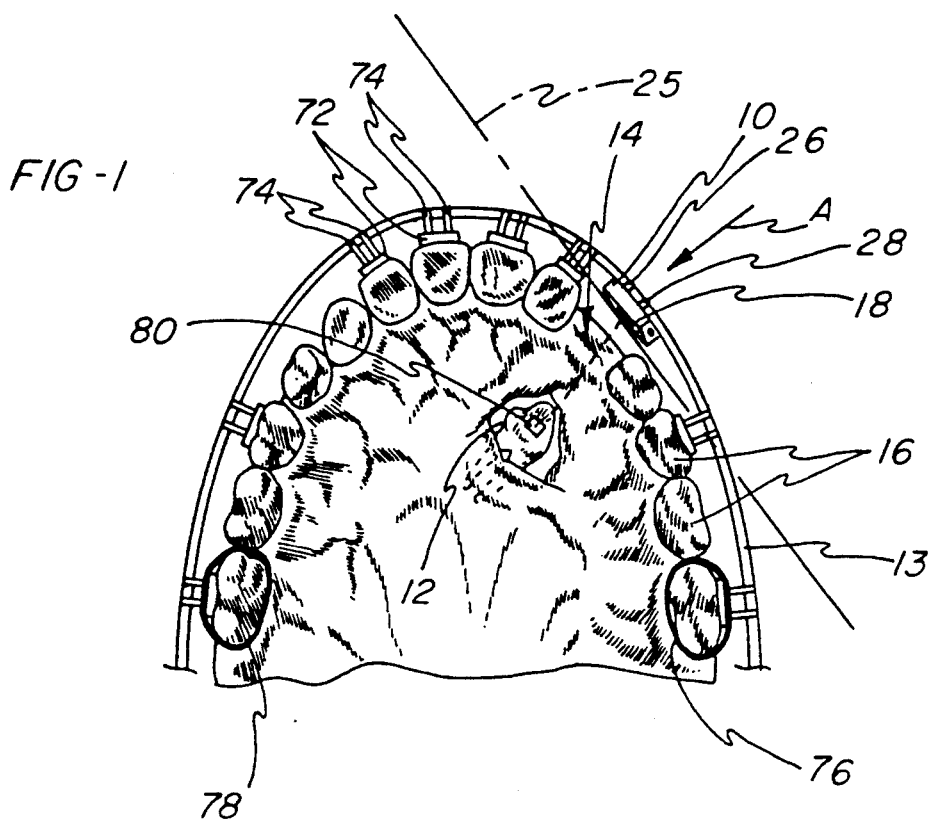
FIG. 1 is a view showing an adjustable aligning reel mounted on an archwire with a filament secured to a misaligned tooth.
Figure 2:
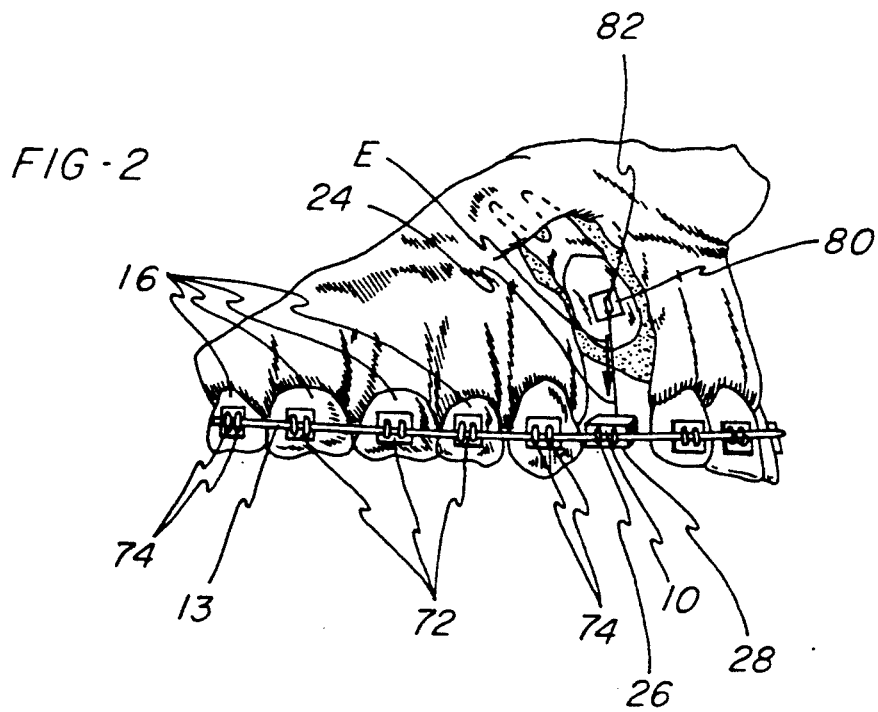
FIG. 2 is a fragmentary view, taken in the direction of arrow A in FIG. 1, showing further details of the adjustable aligning reel mounted on the archwire.

FIG. 1 is a view showing a preferred embodiment of an adjustable aligning reel, designated generally as aligning reel 10, for aligning a misaligned tooth 12 into a predetermined position 14 in an arch of teeth 16. As best illustrated in FIG. 2, the function of the aligning reel 10 is to pull the misaligned tooth 12 in the direction of arrow E in FIG. 2 so as to pull the misaligned tooth 12 into the predetermined position 14. As illustrated in FIGS. 3–8, the aligning reel 10 comprises a housing 18 having a drive shaft 20 rotatably mounted therein. As best shown in FIG. 3, a side 18a of the housing 18 includes a filament aperture 22 for permitting a filament 24 to pass from the drive shaft 20 to the misaligned tooth 12.

As best illustrated in FIGS. 6–8, a second side 18B of the housing 18 includes a fastener or mounting means for mounting the housing on the archwire 13 in operative relationship to the arch of teeth 16. In the embodiment being described, the mounting means comprises a first tie wing 26 (FIG. 7) and a second tie wing 28 which are conventionally secured or integrally formed as part of the housing 18.

The aligning reel 10 also comprises an adjustable tensioner or adjustable tension means 17 (FIG. 4) is located in the housing 18 for moving the misaligned tooth 12 towards the predetermined position 14. The adjustable tension means 17 is adjustably rotatable so as to reel or winch the filament 24 into the housing 18 so that the misaligned tooth 12 is moved in a direction which is generally transverse an imaginary tangent line 25 (FIG. 1) of the arch of teeth 16.

Figure 9:
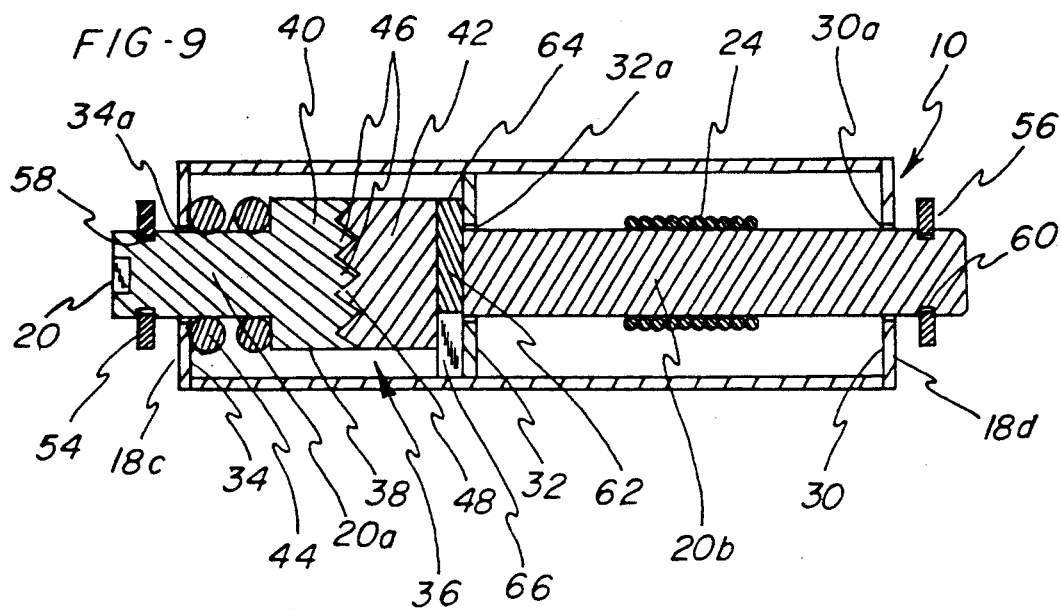
FIG. 9 is a sectional view, taken along the line 9—9 in FIG. 3.

The adjustable tension means 17 also comprises the drive shaft 20 which is rotatably mounted in a first wall 30, a second wall 32, and a third wall 34, as best illustrated in FIG. 9. The first, second, and third walls 30, 32 and 34 each have apertures 30a, 32a, and 34a, for receiving the drive shaft 20 and for permitting the drive shaft 20 to rotate in the housing 18. After the aligning reel 10 is mounted on the archwire 13, the axis of the drive shaft 20 is generally parallel to the imaginary tangent line 25. In the embodiment being described, the drive shaft 20 is a two-piece construction having a first drive end 20a (FIG. 9) and a second drive end 20b. As best illustrated in FIG. 9, the first drive end 20a is received in the first end 18c of the housing 18. The second drive end 20b is rotatably mounted in the apertures 30a and 32b towards the second end 18d of the housing 18.

As illustrated in FIGS. 4, 5 and 9, the adjustable tension means 17 further comprises protection means for ensuring that the predetermined tension does not exceed a preselected tension limit. In the embodiment being described, the protection means includes a slip gear portion 36. The slip gear portion 36 comprises a first gear member 30a which is integrally formed as part of the first drive portion 20a. The slip gear portion 36 comprises a first gear member 40 which is integrally formed as part of the first drive portion 20a. The slip gear portion 36 also comprises a second gear member 42 which is integrally formed as part of the second drive portion 20b. The second gear member 42 mates with the first gear member 40 to permit the second drive portion 20b to wind or reel the filament 24 around the second drive portion 20b when the drive shaft 20 is rotated.

The slip gear portion 36 also comprises a spring member 44 for biasing the first gear portion 38 into driven engagement with the second gear member 42. In one embodiment of the invention, the biasing member 44 is a spring which exerts a predetermined force on the first gear member 40 such that the drive shaft 20 can be rotated counterclockwise (when viewed in the direction of arrow C in FIG. 4) until a preselected tension limit is reached. The walls of the gear teeth 46 on the first gear portion 40 ride along the walls of the gear teeth 48 of the second gear member 42 until the spring is compressed, as best shown in FIG. 5. This permits, for example, the gear tooth 46a to move from a first recess 50 (FIG. 5) to a second recess 52. Thus, the slip gear portion 36 permits the first and second gear members 40 and 42 to slip with respect to each other when the tension applied to the misaligned tooth 12 exceeds the preselected tension limit. In the embodiment being described, the preselected tension limit is approximately 50 grams, and the predetermined force of the spring is approximately 25 grams.

As best shown in FIGS. 4-7, the aligning reel 10 further comprises a first C-clip 54 and a second C-clip 56 which are received in the slots 58 and 60, respectively. The function of the C-clips 54 and 56 is to prevent the drive shaft 20 from moving laterally in the housing 18.

The aligner reel 10 also comprises locking means 62 for preventing the filament 24 from unwinding from the drive shaft 20. The locking means 62 prevents the drive shaft 20 from rotating in a counterclockwise direction (as viewed in the direction of arrow C in FIG. 4) so as to cause the filament to be unwound from the second drive portion 20b. The locking means 62 also facilitates maintaining the tension on the misaligned tooth 12 as the filament 24 is winched into the housing 18. In the embodiment being described, the locking means 62 comprises a ratchet 64 and pawl 66, as best shown in FIG. 8. The ratchet 66 is integrally formed as part of the second drive portion 20 of the drive shaft 20b. The pawl 66 is conventionally secured to the housing 18. The ratchet 64 and pawl 66 permit the drive shaft to rotate in only the counterclockwise direction in order to winch the filament 24 into the housing 18 and onto the second drive portion 20b of the drive shaft 20.

Figure 10:
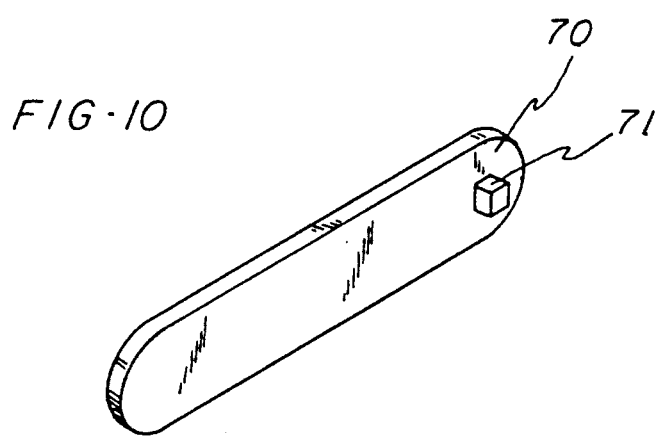
FIG. 10 is a perspective view of a tool which may be used with the keyhole to turn the drive shaft.

The aligning reel 10 also comprises a key hole or key portion 68 for enabling the drive shaft 20 to be rotated, for example, in the counterclockwise direction. The key portion 68 receives a complementary key 71 of a wrench or tool, such as the tool 70 shown in FIG. 10.

The operation of the aligning reel 10 will now be described. The archwire 13 (FIGS. 1 and 2) is conventionally mounted on the arch of teeth 16, for example, with a plurality of brackets 72 which are conventionally mounted to the teeth 16. The plurality of brackets 72 have eyelets 74 for receiving the archwire 13. A pair of closed metal loops 76 and 78 (FIG. 4) are used to facilitate firmly securing the archwire 13 on the arch of teeth 16. Once the archwire 13 is secured on the arch of teeth 16, the aligning reel 10 is mounted onto the archwire 13 using the first and second tie wings 26 and 28 so that the filament aperture 22 is in operative relationship with the misaligned tooth 12. It is to be noted that when the aligning reel 10 is mounted on the archwire 13, the axis of the drive shaft 20 is generally parallel to the imaginary tangent line 25 (FIG. 1) of the archwire 13. This facilitates pulling or winching the misaligned tooth 12 in a direction which is transverse the imaginary tangent line 15 of the arch of teeth 16. A bracket 80 (FIG. 2) is conventionally secured to the misaligned tooth 12 and the filament 24 is tied to an eyelet 82 on the bracket 80. If the misaligned tooth 12 is impacted, it may be necessary to surgically expose the misaligned tooth 12 so that the bracket 80 can be conventionally secured thereto.

After an end of the filament 24 is tied to the eyelet 82 on the bracket 80, a key 71 (FIG. 10) on the tool 70 can be inserted into the key portion 68 of the shaft 20. The tool 70 can then be used to rotate the drive shaft 20 in a counterclockwise direction (as viewed in the direction of arrow C in FIG. 4) so that the filament 24 winches or pulls the misaligned tooth 12 towards the predetermined position 14 with a predetermined amount of tension. In the embodiment being described, the predetermined amount of tension is approximately 25 grams.

The drive shaft 20 can be incrementally rotated in order to winch the filament 24 until the predetermined tension is applied to the misaligned tooth 12. If the drive shaft 20 is rotated such that the tension applied to the misaligned tooth 12 exceeds the predetermined tension limit mentioned earlier herein, then the slip gear portion 36 will enable the first drive portion 20a to rotate in the counterclockwise direction while the second drive portion 20B remains stationary. This ensures that an excessive amount of tension or pressure will not be used to pull the misaligned tooth 12 towards the predetermined position 14. By incrementally rotating the drive shaft 20 over a period of time with the predetermined amount of tension, the misaligned tooth 12 can be quickly moved over a period of time into proper position in the arch of teeth 16.

Advantageously then, the aligning reel 10 permits the orthodontist or even the patient to easily apply a predetermined amount of tension to the misaligned tooth 12. Patients can be taught to use the tool 70 (FIG. 10) to reel or winch the filament 24 in the housing 18, thereby reducing the frequency of orthodontic office visits.

While the invention has been described with reference to a specific embodiment, this description is merely illustrative, and it is not to be construed as limiting the scope of the invention. For example, the protection means has been shown to include the slip gear portion 36, but it could include any suitable means for preventing the aligning reel 10 from applying more than the preselected tension limit on the filament 24 and misaligned tooth 12. Likewise, although the locking means 62 has been shown and described as including the ratchet and pawl mechanism, it could include any suitable means for preventing the drive shaft 20 from rotating such that the tension on the misaligned tooth 12 is less than the predetermined tension. Although not shown, the pawl mechanism could be replaced with a switch (not shown) for permitting the ratchet wheel 64 and drive shaft 20 to rotate in the clockwise direction (as viewed in the direction of arrow C in FIG. 4). This would facilitate unwinding the filament 24 out of the housing, for example, when the aligning reel 10 is mounted on the archwire 13 or when the aligning reel is being sterilized for reuse. In addition, the biasing means has been shown to include the spring 44, but it could comprise any suitable means for biasing the first gear member 46 of the slip gear portion 36 into operative engagement with the second gear member 48. Various other modifications and changes may occur to those skilled in the art without departing from the true spirit and scope of the invention as defined by the appended claims.

I claim:

1. An adjustable aligning reel for aligning a tooth into a predetermined position in an arch of teeth, said adjustable aligning reel comprising:
    an adjustable tensioner which is capable of being mounted on an archwire in operative relationship with the tooth; and
    a filament for coupling the tooth to said adjustable tensioner;
    said adjustable tensioner being adjustable to cause the filament to apply a predetermined tension to the tooth in order to maneuver the tooth towards the predetermined position;
    said adjustable tensioner further comprising protection means for ensuring that the predetermined tension does not exceed a preselected tension limit.

2. The adjustable aligning reel as recited in claim 1 wherein said adjustable tensioner further comprises a housing having a drive shaft rotatably mounted therein, said filament being secured to said drive shaft such that, upon rotation of said drive shaft, said filament is winched therearound, thereby causing said filament to pull said misaligned tooth toward said predetermined position.

3. The adjustable aligning reel as recited in claim 1 wherein said protection means comprises a slip gear.

4. An adjustable aligning reel for aligning a tooth into a predetermined position in an arch of teeth, said adjustable aligning reel comprising:
    an adjustable tensioner which is capable of being mounted on an archwire in operative relationship with the tooth; and
    a filament for coupling the tooth to said adjustable tensioner;
    said adjustable tensioner being adjustable to cause the filament to apply a predetermined tension to the tooth in order to maneuver the tooth towards the predetermined position;
    said adjustable tensioner further comprising a housing having a drive shaft rotatably mounted therein, said filament being secured to said drive shaft such that, upon rotation of said drive shaft, said filament is winched therearound, thereby causing said filament to pull said misaligned tooth toward said predetermined position;
    said drive shaft having a slip gear portion for ensuring that said predetermined tension does not exceed a preselected tension limit.

5. The adjustable aligning reel as recited in claim 4 wherein said predetermined tension is less than 50 grams.

6. The adjustable aligning reel as recited in claim 4 wherein said housing has a first end and a second end, said drive shaft having a first drive end rotatably mounted in said first end and a second drive end rotatably mounted in said second end; said first drive end having a key portion for enabling said drive shaft to be rotated from a first position to a second position 7. The adjustable aligning reel as recited in claim 4 wherein said preselected tension limit is in the order of 50 grams.

8. The adjustable aligning reel as recited in claim 4 wherein said filament is a wire.

9. The adjustable aligning reel as recited in claim 4 wherein said drive shaft comprises a first drive portion and a second drive portion, said slip gear portion comprising a first gear member and a second gear member, said first gear member being secured to said first drive portion and said second gear member being secured to said second drive portion, said slip gear portion further comprising a spring member for biasing said first gear member into driven engagement with said second gear member.

10. The adjustable aligning reel as recited in claim 4 wherein said adjustable tension reel moves said filament so that said tooth moves in a direction which is transverse a tangent line of said arch of teeth.

11. The adjustable aligning reel as recited in claim 4 wherein the axis of said drive shaft is generally parallel to the tangent line of said archwire when said adjustable aligning reel is mounted thereon.

12. An adjustable aligning reel for aligning a tooth into a predetermined position in an arch of teeth, said adjustable aligning reel comprising:
    an adjustable tensioner which is capable of being mounted on an archwire in operative relationship with the tooth; and
    a filament for coupling the tooth to said adjustable tensioner;
    said adjustable tensioner being adjustable to cause the filament to apply a predetermined tension to the tooth in order to maneuver the tooth towards the predetermined position;

said adjustable tensioner further comprising a housing having a drive shaft rotatably mounted therein, said filament being secured to said drive shaft such that, upon rotation of said drive shaft, said filament is winched therearound, thereby causing said filament to pull said misaligned tooth toward said predetermined position; and said adjustable aligning reel comprising locking means for preventing the filament from unwinding.

13. The adjustable aligning reel as recited in claim 12 wherein said locking means comprises a ratchet and pawl mechanism.

14. An aligning reel for aligning a misaligned tooth into a predetermined position in an arch of teeth, said aligning reel comprising:

a housing;

mounting means for mounting said housing on an archwire which is positioned in operative relationship to said arch of teeth;

adjustable tension means located in said housing for moving the misaligned tooth towards the predetermined position;

a filament for coupling the misaligned tooth to said adjustable tension means;

said adjustable tension means being adjustably rotatable to reel said filament so that said misaligned tooth is moved towards the predetermined position;

said adjustable tension means moving said filament so that said misaligned tooth moves in a direction which is transverse a tangent line of said arch of teeth;

said adjustable tension means comprising a drive shaft rotatably mounted in said housing;

said housing having a filament aperture for permitting said filament to pass from said drive shaft to said misaligned tooth; and said adjustable tension means further comprising protection means for ensuring that the predetermined tension does not exceed a preselected tension limit.

15. The aligning reel as recited in claim 14 wherein said adjustable tension means comprises a drive shaft rotatably mounted in said housing, said housing having a filament aperture for permitting said filament to pass from said drive shaft to said misaligned tooth.

16. The aligning reel as recited in claim 14 wherein the axis of said drive shaft is generally parallel to the tangent line of said archwire when said aligning reel is mounted on said archwire.

17. The aligning reel as recited in claim 14 wherein said housing has a first end and a second end, said drive shaft having a first drive end rotatably mounted in said first end and a second drive end rotatably mounted in said second end; said first drive end having a key portion for enabling said drive shaft to be rotated from a first position to a second position.

18. The aligning reel as recited in claim 14 wherein said drive shaft is rotatably mounted in said housing using at least one C-clip.

19. The aligning reel as recited in claim 14 wherein said preselected tension limit is in the order of 50 grams.

20. The adjustable aligning reel as recited in claim 14 wherein the filament is a wire.

21. The adjustable aligning reel as recited in claim 14 wherein said protection means includes a slip gear.

22. The aligning reel as recited in claim 14 wherein said mounting means comprises a plurality of wings.

23. The aligning reel as recited in claim 14 wherein said protection means comprises a slip gear.

24. An aligning reel for aligning a misaligned tooth into a predetermined position in an arch of teeth, said aligning reel comprising:

a housing;

mounting means for mounting said housing on an archwire which is positioned in operative relationship to said arch of teeth;

adjustable tension means located in said housing for moving the misaligned tooth towards the predetermined position;

a filament for coupling the misaligned tooth to said adjustable tension means;

said adjustable tension means being adjustably rotatable to reel said filament so that said misaligned tooth is moved towards the predetermined position;

said adjustable tension means moving said filament so that said misaligned tooth moves in a direction which is transverse a tangent line of said arch of teeth;

said adjustable tension means comprising a drive shaft rotatably mounted in said housing;

said housing having a filament aperture for permitting said filament to pass from said drive shaft to said misaligned tooth;

said aligning reel further comprising a locking mechanism to prevent the filament from unwinding.

25. The aligning reel as recited in claim 24 wherein said locking mechanism comprises a ratchet and pawl.

26. An aligning reel for aligning an impacted tooth into a predetermined position in an arch of teeth, said arch of teeth having an arch wire operatively mounted thereon; said aligning reel comprising:

a housing;

a fastener located on said housing for fastening the housing to the arch wire;

a drive shaft rotatably mounted in said housing;

a locking mechanism for permitting said drive shaft to rotate in a first direction and also for restricting movement of said drive shaft in a direction opposite said first direction; and a filament for coupling said drive shaft to said impacted tooth;

when said housing is mounted on the arch wire and said filament is coupled to said impacted tooth, said drive shaft may be adjustably rotated in said first direction, thereby causing said filament to be tightened to a predetermined tension in order to pull the impacted tooth towards said predetermined position.

27. The aligning reel as recited in claim 26 wherein said drive shaft can be winched to move said filament so that said impacted tooth moves in a direction which is transverse a tangent line of said arch of teeth.

28. The aligning reel as recited in claim 26 wherein said housing is generally rectangular and has a filament aperture for permitting said filament to pass from said drive shaft to said impacted tooth; said drive shaft having an axis which is generally parallel to said tangent line of said arch of teeth.

29. The aligning reel as recited in claim 26 wherein said aligning reel comprises a key portion for enabling said drive shaft to be manually rotated;

said filament being a wire and said preselected tension limit being not greater than 50 grams.

30. An aligning reel for aligning an impacted tooth into a predetermined position in an arch of teeth, said arch of teeth having an arch wire operatively mounted thereon; said aligning reel comprising:
- a housing;
- a fastener located on said housing for fastening the housing to the arch wire;
- a drive shaft rotatably mounted in said housing;
- a locking mechanism for permitting said drive shaft to rotate in a first direction; and
- a filament for coupling said drive shaft to said impacted tooth;
- when said housing is mounted on the archwire and said filament is coupled to said impacted tooth, said drive shaft may be adjustably rotated in said first direction, thereby causing said filament to be tightened to a predetermined tension in order to pull the impacted tooth towards said predetermined position;
- said locking mechanism comprising a ratchet located on said drive shaft and a pawl located on said housing;
- said aligning reel further comprising a slip gear mounted to said shaft for preventing the tension applied to said drive shaft to exceed a preselected tension limit;
- said drive shaft being rotatably mounted in said housing using at least one C-clip.

31. The adjustable aligning reel as recited in claim 30 wherein said drive shaft comprises a first drive portion and a second drive portion, said slip gear portion comprising a first gear portion located on said first drive portion and a second gear portion located on said second drive portion, said slip gear portion also comprising a spring member for engaging said first drive portion and for biasing said first drive portion into driven engagement with said second drive portion, such that said first gear portion disengages said second gear portion when said preselected tension limit is exceeded.

32. A method of moving a tooth towards a predetermined position in an arch of teeth, said method comprising the steps of:
- (a) mounting an adjustable tension reel on an arch wire associated with said arch of teeth; said adjustable tension reel having a filament which can be reeled into said adjustable tension reel;
- (b) mounting an end of said filament to said tooth;
- (c) reeling said filament in a first direction into said adjustable tension reel so as to move said tooth towards said predetermined position; and
- (d) locking said adjustable tension reel so that said filament does not unwind in a direction opposite said first direction.

33. The method as recited in claim 32 wherein said adjustable tension reel comprises a drive shaft rotatably mounted therein, said drive shaft having an end having a keyhole therein; said reeling step (c) including the step of:
- (c)(1) inserting a key in said key hole and rotating said drive shaft so as to cause said filament to pull said tooth towards said predetermined position.

34. The method as recited in claim 32 wherein said method further comprises the step of:
- (e) repeating steps (a)–(d) over a period of time until said tooth is properly aligned in said arch of teeth.

* * * * *

UNITED STATES PATENT AND TRADEMARK OFFICE
CERTIFICATE OF CORRECTION

PATENT NO. : 5,292,249
DATED     : March 8, 1994
INVENTOR(S) : Daniel S. German

It is certified that error appears in the above-identified patent and that said Letters Patent is hereby corrected as shown below:

Claim 6, Col. 6, line 35, please add a period after the last word in the paragraph.

Signed and Sealed this

Ninth Day of August, 1994

Attest:

BRUCE LEHMAN

Attesting Officer

Commissioner of Patents and Trademarks